(12) United States Patent
Joo et al.

(10) Patent No.: US 6,198,001 B1
(45) Date of Patent: Mar. 6, 2001

(54) MANUFACTURING METHOD FOR 4-NITROSOANILINE FROM UREA AND NITROBENZENE

(75) Inventors: Young J. Joo; Jin-Eok Kim; Jeong-Im Won; Kum-Ui Hwang, all of Taejeon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/525,834

(22) Filed: Mar. 15, 2000

(30) Foreign Application Priority Data

Nov. 16, 1999 (KR) .................................................. 99-50965

(51) Int. Cl.[7] .................................................... C07C 15/42

(52) U.S. Cl. ............................................................ 564/414

(58) Field of Search ............................................... 564/414

(56) References Cited

U.S. PATENT DOCUMENTS 3,338,966 * 8/1967 Snyder .................................. 564/402
5,380,946 * 1/1995 Stern et al. ........................... 564/124

* cited by examiner

*Primary Examiner*—Samuel Barts
(74) *Attorney, Agent, or Firm*—Harrison & Egbert

(57) ABSTRACT

A method for preparing 4-nitrosoaniline, including reacting urea and nitrobenzene in a polar organic solvent in the presence of a base at a temperature of room temperature to 150° C. The method uses a relatively cheap urea and nitrobenzene as the raw materials, and also a relatively cheap base, thereby decreasing the manufacturing cost. Urea used as an amine donor is excellent in a reactivity to nitrobenzene, and a reaction intermediate is unstable as compared with 4-(4-nitrophenyl)benzamide to easily decompose into 4-nitroaniline and 4-nitrosoaniline. This allows a reaction time and a process time to be shortened. Moreover, the method is advantageous in that waste hazardous to the environment is not produced as a byproduct.

6 Claims, No Drawings

MANUFACTURING METHOD FOR 4-NITROSOANILINE FROM UREA AND NITROBENZENE

TECHNICAL FIELD

The present invention relates to methods for preparing 4-nitrosoaniline and, more particularly, relates to a method of selectively preparing 4-nitrosoaniline wherein urea is reacted with nitrobenzene in a polar organic solvent in the presence of a base.

BACKGROUND ART

4-Nitrosoaniline is used in some applications, such as an intermediate for the preparation of dyestuffs or for the preparation of a hair dye, and as a light stabilizer. However, it had not been greatly studied in its applications, due to a difficulty in its preparation.

It is known to prepare 4-nitrosoaniline by synthesizing N-nitrosoaniline from aniline and sodium nitrite ($NaNo_2$) and subsequent Fischer-Hepp rearrangement (Tetrahedron, 1975, 31, 1343–9, and U.S. Pat. No. 3,338,966). This method is disadvantageous because a denitrososation occurs during the Fischer-Hepp rearrangement, and waste containing nitroso (NO) compounds harmful to the environment can be generated in great quantities.

It is also known to prepare 4-nitrosoaniline by reaction of p-nitrosophenol and ammonia or ammonium chloride (J. Chem. Soc., 1955, 2049). This method is disadvantageous because the yield of 4-nitrosoaniline is too low.

Recently, it is found that 4-nitrodiphenylamine (4-NDPA), a precursor of 4-aminodiphenylamine which is utilized for the preparation for antiozonants for rubber, is produced by reacting aniline and nitrobenzene in the presence of a base via a nucleophilic aromatic substitution for hydrogen (NASH). Compared with other methods for preparing 4-NDPA, the NASH process provides dramatic reductions (90% or more) in generated chemical waste and wastewater, eliminates the use of an environmentally unfavorable chemical (chlorine), and improves process safety. In addition, this method is advantageous in that a process for separating 4-chloronitrobenzene from an isomer mixture is not required, and also the purity of a final product is extremely high.

Among reactions of using the NASH, it is well-known to prepare 4-NDPA and 4-nitrosodiphenylamine (4-NODPA) by a direct reaction of aniline with nitrobenzene in the presence of tetramethylammonium hydroxide (TMA(OH)). See, J. Am. Chem. Soc., 1992, 114(23), 9237–8; U.S. Pat. No. 5,117,063; U.S. Pat. No. 5,253,737; U.S. Pat. No. 5,331,099; U.S. Pat. No. 5,453,541; U.S. Pat. No. 5,552,531; and U.S. Pat. No. 5,633,407.

It is reported that the ratio of 4-NDPA and 4-NODPA produced in the reaction can be controlled by the molar ratio of aniline to nitrobenzene. For example, where a molar ratio of aniline to nitrobenzene is about 1, yield of 4-NODPA and 4-NDPA are shown to be 15 mole % and 80 mole %, respectively. On the other hand, where a molar ratio of aniline to nitrobenzene is about 50, 4-NODPA and 4-NDPA are obtained in yields of 86 mole % and 9 mole %. The selectivity to final products is known to be dependent on whether a hydride ion ($H^-$) of an intermediate product formed from aniline and nitrobenzene is leaving via an intramolecular reaction or an intermolecular reaction.

It is also known to prepare 4-nitrosoaniline from nitrobenzene and benzamide in the NASH reaction. This is carried out by a two step reaction consisting of synthesizing N-(4-nitrophenyl)benzamide as a stable intermediate, and then adding water(or ammonia) to decompose the product into 4-nitroaniline and benzoic acid (or benzamide). See, J. Am. Chem. Soc., 1992, 114(23); J. Org. Chem., 1993, 58, 6883–6888; U.S. Pat. No. 5,436,371; U.S. Pat. No. 5,380,946; and PCT publication WO 93/24447. In the reaction, the yield of N-(4-nitrophenyl)benzamide is about 98% when moisture was completely removed, whereas the yield of N-(4-nitrophenyl)benzamide is only about 20% when prepared under an oxygen atmosphere without removal of moisture. From these results, it was shown that making a moisture-free reaction condition was particularly important. Moreover, this reaction was reported to produce 4-nitroaniline without referring to the production of 4-nitrosoaniline.

Meanwhile, 4-nitrosoaniline is subjected to a hydrogenation process to produce p-phenylenediamine (PPD). PPD is broadly used as a raw material for cosmetics and antioxidants, and additives to fuel, and also has a great utility in a dye application due to its property of being capable of being easily oxidized to form a colorant. Also, PPD has the greatest utility for manufacturing aramid as a functional fiber that has high chemical resistance, high thermal resistance and high strength, as well as for producing phenylene diisocyanate that is a raw material for polyurethane.

SUMMARY OF THE INVENTION

Diligent efforts have been made to find an improved method for preparing 4-nitrosoaniline, as compared with the prior methods' problem. Such as when a nitroso compound hazardous to the environment is produced as a byproduct after the reaction, a reaction is very difficult to produce, and also the yield of 4-nitrosoaniline is low. As a result, it is found that a direct reaction of urea with nitrobenzene in the presence of a base could produce 4-nitrosoaniline, and it is also found that, when using an alkali metal or an alkaline earth metal as the base and appropriately controlling the amount of urea and nitrobenzene used, 4-nitrosoaniline could be produced in a high yield and selectivity, whereby the present invention was achieved.

The present invention is advantageous in that 4-nitrosoaniline can be produced in high yield with little or no ortho compounds, such as 2-nitroaniline and 2-nitrosoaniline, and hydrogenated to PPD with high purity. Moreover, the present invention is useful in that a reaction is not influenced by moisture content to a great degree, and it is not necessary to make a reaction condition moisture-free. Additionally, the method has an advantage because a two step reaction, in which an intermediate is formed and then decomposed, is not performed, such that the reaction can be achieved in one reactor in a short period of time.

DETAILED DESCRIPTION OF THE INVENTION

The foregoing and other objects, features and advantages of the invention will be apparent to those skilled in the art to which the present invention relates from reading the following specification.

The present invention relates to a method of preparing 4-nitrosoaniline from urea and nitrobenzene in a polar organic solvent in the presence of a general base.

The present invention applies the NASH reaction to producing selectively 4-nitrosoaniline under mild conditions as compared with those of the prior method, by reacting urea with nitrobenzene in the presence of a cheap alkali metal base.

Urea, that can easily lose a proton in the presence of a base, is excellent in a reactivity with nitrobenzene, and is not substantially influenced by moisture content. Moreover, a product of urea and nitrobenzene is unstable, such that it is easily decomposed into 4-nitroaniline and 4-nitrosoaniline by moisture generated during a reaction. This allows the reaction time and the process time to be shortened.

In accordance with the present invention, an appropriate control of a molar ratio of nitrobenzene/urea can play a critical role in a selectivity to a final product. Where a molar ratio of nitrobenzene/urea is in excess of 1, main products are mainly 4-nitroaniline and 4,4'-dinitrodiphenylamine (hereinafter, called "DNDPA"). However, where a molar ratio of nitrobenzene/urea is less than 1, a main product is 4-nitrosoaniline.

A variety of polar organic solvents can be used in the practice of the present invention. Among these solvents, examples of the polar organic solvents, preferred in view of a miscibility with the base, include, but are not limited to, dimethylsulfoxide (hereinafter, called "DMSO"), N,N-dimethylformamide (hereinafter, called "DMF"), and N-methyl-2-pyrrolidinone (hereinafter, called "NMP"). A reaction in DMSO results in the highest reactivity and yield. The weight ratio of the solvent to urea used is in the range of about 50:1 to about 1:1, with the preferred ratio being in the range of about 30:1 to about 1:1.

Examples of the base used in accordance with the present invention include, but are not limited to, alkali metal and alkaline earth metal bases, such as sodium hydroxide (NaOH), potassium hydroxide (KOH), potassium t-butoxide (t-BuOK), and sodium hydride (NaH), and TMA(OH). The molar ratio of the base to urea used is in the range of about 1:1 to about 10:1, with the preferred ratio being in the range of about 1:1 to about 4:1.

The amount of nitrobenzene used in accordance with the present invention has a great effect on a selectivity of the final product. A molar ratio of nitrobenzene to urea used in excess of 1 increases a selectivity to 4-nitroaniline and accelerates a production of DNDPA. On the other hand, a molar ratio of nitrobenzene to urea less than 1 results in an excellent selectivity to 4-nitrosoaniline.

To remove moisture produced upon the beginning of or during the reaction from the reaction solution, a vacuum distillation is performed, or a drying agent is used. Materials useful as the drying agent, include anhydrous calcium carbonate, anhydrous sodium sulfate, anhydrous magnesium sulfate, sodium hydroxide, potassium hydroxide, sodium hydride, molecular sieve, and the like. However, as the method of the present invention is not influenced by the amount of moisture to a great degree during the reaction, the use of the drying agent or a continuous distillation to remove moisture from the reaction solution results in a little increase in yield. The reaction can be carried out under a nitrogen or oxygen atmosphere or in the air. Additionally, a molar ratio of the moisture to the base in excess of 3 results in a decrease in a reaction rate.

The reaction in accordance with the present invention is carried out under an atmosphere through which oxygen or nitrogen is passed. Under the nitrogen atmosphere, there is produced a byproduct, such as azobenzene, azoxybenzene and the like. However, in the case that a molar ratio of nitrobenzene/urea is less than 1, the reaction is not influenced by the atmosphere, and produces azoxybenzene in the amount of 1% even under the nitrogen atmosphere.

EXAMPLES

The following examples are for illustration purposes only and in no way limit the scope of this invention.

In the following examples, products were analyzed by the Nuclear Magnetic Resonance (NMR) spectrum and the Gas Chromatography/Mass Selective Detector to identify them. Also, the products were analyzed by gas chromatography and high performance liquid chromatography to determine their quantitative analysis values. In this quantitative analysis, all the materials except for DNDPA were analyzed by gas chromatography, and analysis conditions were as follows:

| | |
|---|---|
| Capillary column: | ULTRA 2 (Crosslinked 5% Ph Me Silicon) 50 m × 0.2 mm × 0.33 μm. |
| Carrier gas: | nitrogen |
| Head pressure: | 20 psig |
| Oven: | 150° C. (2 min.) to 280° C., β = 10° C./min. |
| Detector and temperature: | FID (280° C.) |
| Split ratio: | 30:1 |
| Make up gas flow rate: | 38 ml. |

As DNDPA is a material unsuitable to be analyzed by gas chromatography due to its high boiling point, it was quantitatively analyzed using high performance liquid chromatography. Such a high performance liquid chromatography was carried out using a product manufactured by Hitachi Co. in Japan and consisting of L-6200 intelligent pump and L-4200 UV-VIS detector. In high performance liquid chromatography, all quantitative values were measured at a wavelength of 254 nm, and elution rate was 1 ml/minute. Furthermore, in high performance liquid chromatography, a Cosmosil 5C18-AR (4.6×150 mm) packed column was used. An elution gradient of high performance liquid chromatography is shown in Table 1 below.

TABLE 1

Elution gradient of HPLC

| | Elution gradient | |
|---|---|---|
| Time (minute) | Solvent A<br>% Distilled water | Solvent B<br>% Acetonitrile |
| 0 | 65 | 35 |
| 25 | 0 | 100 |
| 33 | 65 | 35 |

For the quantitative analysis of each product, pyrene was used as an internal standard. An area ratio for a concentration of each material was calculated relative to an area of pyrene and standard-calibrated. A molar concentration of a product was calculated from the calibration curve, and a yield was based on nitrobenzene.

EXAMPLE 1

A 100 ml three-neck reactor equipped with a condenser and a thermometer was filled with 3.60 g (60 mmol) of urea, 1.50 g of potassium carbonate, 3.96 g (60 mmol) of potassium hydroxide, 0.3034 g of pyrene, and 25 g of DMSO. Then, the resulting mixture was heated to 90° C. while stirring under an oxygen atmosphere. Once the reaction temperature reached 90° C., a mixed solution of 2.48 g (20 mmol) of nitrobenzene and 5 g of DMSO was slowly added dropwise over a period of time of 5 to 10 minutes via a syringe. Then, a temperature was cautioned to keep 90±4° C. while adding a nitrobenzene solution. For a quantitative analysis, a sample was taken out and dissolved in 2.5 ml of ethyl acetate containing a small amount of water, and moisture was then removed from the resulting solution with magnesium sulfate ($MgSO_4$). The quantitative analysis has shown that 4-nitrosoaniline and 4-nitroaniline were obtained in yields of 87 mole % and 12 mole %, respectively, based on nitrobenzene.

COMPARATIVE EXAMPLE 1

A 100 ml three-neck reactor equipped with a condenser and a thermometer was filled with 7.32 g (60 mmol) of benzamide, 1.50 g of potassium carbonate, 3.96 g (60 mmol) of potassium hydroxide, 0.3034 g of pyrene, and 25 g of DMSO. Next, the resulting mixture was stirred under oxygen, and then heated to 90° C. Once the reaction temperature reached 90° C., a mixed solution of 2.48 g (20 mmol) of nitrobenzene and 5 g of DMSO was slowly added dropwise over a period of time of 5 to 10 minutes via a syringe. After reacting for 2 hours, a sample was taken out, and dissolved in 2.5 ml of ethyl acetate. Then, moisture of the resulting solution was removed with magnesium sulfate ($H_2SO_4$). A quantitative analysis of the product by GC has indicated that 4-nitrosoaniline and 4-nitroaniline were obtained in yields of 14 mole % and 1 mole %, respectively, based on nitrobenzene, and an intermediate N-(4-nitrophenyl)benzamide was also obtained. For the identification of a production of N-(4-nitrophenyl)benzamide, the reaction solution was treated with hexane, added with 5 g of water and 30 g of DMSO, and then left to react at a temperature of 80 to 90° C. for 8 hours. After that, a sample was taken out, and dissolved in 2.5 ml of ethyl acetate. Then, moisture in the resulting solution was removed with magnesium sulfate ($H_2SO_4$). A quantitative analysis of the resulting material has shown that 4-nitroaniline was obtained in an yield of 26 mole % based on nitrobenzene.

EXAMPLE 2

Reactions were carried out under the same conditions as those in Example 1 except that a reaction temperature for each reaction was changed. Results are shown in Table 2 below.

TABLE 2

| Reaction temperature (° C.) | Conversion (mole %) Nitrobenzene | Yield (mole %) 4-Nitrosoaniline | 4-Nitroaniline | DNDPA* |
|---|---|---|---|---|
| 50 | 65 | 28 | 18 | — |
| 70 | 97 | 75 | 12 | 9 |
| 90 | 100 | 87 | 12 | — |
| 130 | 35 | 4 | 2 | — |

*Yield obtained by liquid chromatography.

EXAMPLE 3

Reactions were carried out under the same conditions as those in Example 1 except that a molar ratio of nitrobenzene to urea for each reaction was changed. Results are shown in Table 3 below.

TABLE 3

| Nitrobenzene/Urea | Conversion (mole %) Nitrobenzene | Yield (mole %) 4-Nitrosoaniline | 4-Nitroaniline |
|---|---|---|---|
| 1/5 | 100 | 87(18)* | 12(2) |
| 1/4 | 100 | 86(22) | 13(3) |
| 1/3 | 100 | 87(27) | 12(5) |
| 1/2 | 98 | 59(29) | 13(6) |
| 1 | 64 | 18(18) | 8(8) |

*Yield based on urea.

EXAMPLE 4

Reactions were carried out under the same conditions as those in Example 1 except that a kind of base for each reaction was changed. Results are shown in Table 4 below.

TABLE 4

| Base | Conversion (mole %) Nitrobenzene | Yield (mole %) 4-Nitrosoaniline | 4-Nitroaniline | DNDPA |
|---|---|---|---|---|
| Sodium hydroxide | 100 | 62 | 14 | 5 |
| Potassium hydroxide | 100 | 87 | 12 | — |
| TBuOK | 100 | 35 | 16 | — |
| TMA(OH) | 100 | 94 | 6 | — |

EXAMPLE 5

A 100 ml three-neck reactor equipped with a condenser and a thermometer was filled with 1.20 g (20 mmol) of urea, 2 g of potassium carbonate, 0.1011 g of pyrene, 25 g of DMSO, and KOH of a molar ratio varying to urea shown in Table 5. Then, the resulting mixture was allowed to stir while heating to a temperature of 90° C. Once the reaction temperature reached 90° C., a mixed solution of 0.83 g (6.7 mmol) and 5 g of DMSO was slowly added dropwise over a period of time of 5 to 10 minutes via a syringe. The resulting mixture was left to react for 2 hours while a temperature inside of the reactor did not exceed 90±4° C. Then, a quantitative analysis of the product was carried out. Results are shown in Table 5 below.

TABLE 5

| KOH/Urea | Conversion (mole %) Nitrobenzene | Yield (mole %) 4-Nitrosoaniline | 4-Nitroaniline |
|---|---|---|---|
| 1 | 94 | 44 | 13 |
| 2 | 100 | 76 | 14 |
| 4 | 100 | 70 | 17 |
| 6 | 100 | 73 | 16 |

EXAMPLE 6

Reactions were carried out under the same conditions as those in Example 1 except that a kind of solvent for each reaction used was changed. Results are shown in Table 6 below.

TABLE 6

| Solvent | Conversion (mole %) Nitrobenzene | Yield (mole %) 4-Nitrosoaniline | 4-Nitroaniline |
|---|---|---|---|
| DMSO | 100 | 87 | 12 |
| NMP | 90 | 5 | 2 |
| DMF | 0 | 0 | 0 |
| Xylene* | 60 | 19 | 4 |
| Dioxane* | 71 | 32 | 8 |

*Xylene and dioxane were mixed with DMSO, respectively, in the weight ratio of 1:1.

EXAMPLE 7

Reactions were carried out under the same conditions as those in Example 1 except for amounts of solvents used were changed. Results are shown in Table 7 below.

TABLE 7

| DMSO (g) | Conversion (mole %) Nitrobenzene | Yield (mole %) 4-Nitrosoaniline | 4-Nitroaniline |
|---|---|---|---|
| 5 | 100 | 73 | 10 |
| 10 | 100 | 87 | 12 |
| 20 | 100 | 86 | 14 |
| 30 | 88 | 49 | 9 |

EXAMPLE 8

Reactions were carried out under the same conditions as those in Example 1 except that moisture content in a reaction system for each reaction was changed. Results are shown in Table 8 below.

TABLE 8

| Moisture content and drying agent | Conversion (mole %) Nitrobenzene | Yield (mole %) 4-Nitrosoaniline | 4-Nitroaniline | DNDPA |
|---|---|---|---|---|
| Drying agent was not used[A] | 100 | 72 | 11 | — |
| $K_2CO_3$[B] | 100 | 87 | 12 | — |
| Vacuum[C] | 100 | 75 | 11 | 5 |
| Water (1 mole)[D] | 100 | 77 | 13 | 5 |
| Water (3 mole)[E] | 82 | 60 | 8 | 2 |

[A]Commercially available solvent was used without the purification.
[B]Drying agent was used to remove moisture in a reaction system.
[C]A reaction was carried out while removing moisture under a vacuum condition.
[D and E]The used amount of water based on KOH.

EXAMPLE 9

Reaction were carried out under the same conditions as those in Example 1 except that an atmosphere for each reaction was oxygen, nitrogen, and air, respectively. Results are shown in Table 9 below.

TABLE 9

| Atmosphere | Conversion (mole %) Nitrobenzene | Yield (mole %) 4-Nitrosoaniline | 4-Nitroaniline | DNDPA |
|---|---|---|---|---|
| Oxygen | 100 | 87 | 12 | — |
| Nitrogen | 100 | 77 | 10 | — |
| Air | 100 | 75 | 10 | — |

INDUSTRIAL APPLICABILITY

As apparent from the above description, the present invention provides the method for preparing 4-nitrosoaniline in which a relatively cheap urea and nitrobenzene are used as the raw materials, and also a relatively cheap base is used, thereby decreasing a manufacturing cost. In the method in accordance with the present invention, urea used as an amine donor is excellent in a reactivity to nitrobenzene, 4-nitrosoaniline is produced in high yield with little or no ortho compounds, and a reaction intermediate is unstable as compared with 4-(4-nitrophenyl)benzamide to easily decompose into 4-nitroaniline and 4-nitrosoaniline. This allows a reaction time and a process time to be shortened. Moreover, the method of the present invention is advantageous because waste hazardous to the environment is not produced as a byproduct.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

We claim:

1. A method for preparing 4-nitrosoaniline, comprising reacting urea and nitrobenzene in a polar organic solvent in the presence of a base at a temperature of room temperature to 150° C.

2. The method of claim 1, wherein a molar ratio of the nitrobenzene to urea is less than 1.

3. The method of claim 1, wherein the polar organic solvent is selected from the group consisting of dimethylsulfoxide (DMSO), dimethylformamide (DMF), N-methyl-2-pyrrolidinone (NMP), xylene mixed with dimethylsulfoxide, and dioxane mixed with dimethylsulfoxide.

4. The method of claim 1, wherein the base is selected from the group consisting of sodium hydroxide, sodium hydride, potassium hydroxide, potassium t-butoxide, and tetramethylammonium hydroxide.

5. The method of claim 1, wherein a molar ratio of the base to the urea is in the range of 1 to 10.

6. The method of claim 1, wherein the reaction is carried out in a nitrogen, oxygen, or air atmosphere.

* * * * *